(12) United States Patent
Huang et al.

(10) Patent No.: US 8,663,970 B1
(45) Date of Patent: Mar. 4, 2014

(54) RECOMBINANT THERMOTOLERANT YEAST WITH A SUBSTITUTE HEAT SHOCK PROTEIN 104 PROMOTER

(75) Inventors: Kuang-Tse Huang, Chiayi County (TW); Hau-Ren Chen, Chiayi County (TW); Wen-Chien Lee, Chiayi County (TW); Chang-Yu Wu, Chiayi County (TW); Hsin-Cheng Chen, Chiayi County (TW); Yu-Long Wu, Chiayi County (TW); Meng-Tsu Tsai, Chiayi County (TW); Ju-Ping Yeh, Chiayi County (TW); Yu-Wei Liang, Chiayi County (TW); Yu-Shiuan Lai, Chiayi County (TW)

(73) Assignee: National Chung Cheng University, Chiayi County (TW)

( * ) Notice: Subject to any disclaimer, the term of this patent is extended or adjusted under 35 U.S.C. 154(b) by 0 days.

(21) Appl. No.: 13/610,015

(22) Filed: Sep. 11, 2012

(51) Int. Cl.
*C12N 1/00* (2006.01)
*C12N 15/74* (2006.01)

(52) U.S. Cl.
USPC ........................................ 435/254.2; 435/471

(58) Field of Classification Search
None
See application file for complete search history.

(56) References Cited

U.S. PATENT DOCUMENTS

| 2009/0155872 A1 | 6/2009 | Abbas et al. |
| 2010/0062506 A1 | 3/2010 | Yamada et al. |
| 2011/0033907 A1 | 2/2011 | Forrester et al. |

OTHER PUBLICATIONS

Hansen et al., Journal of Biotechnology, 1996, vol. 49, pp. 1-12.*
Kawahata et al., Biosci. Biotechnol. Biochem., 2007, vol. 71, pp. 1616-1620.*
Benjaphokee, et al., "Highly Effecient Bioethanol Production by a *Saccharomyces cerevisiae* Strain With Multiple Stress Tolerance to High Temperature, Acid and Ethanol", N. Biotechnol. 2012, 29; p. 379-386.
Boesl, et al., "The Molecular Chaperone Hsp 104—A Molecular Machine for Protein Disaggregation", J. Struct. Biol. 2006, 156; p. 139-148.
Edgardo, et al, "Selection of Thermotolerant Yeast Strains *Saccharomyces cerevisiae* for Bioethanol Production", Enzym. Microb. Tech., 2008, 43; p. 120-123.
Lee, et al., "The Structure of ClpB: A Molecular Chaperone That Rescues Proteins From an Aggregated State", Cell, 2003, 115; p. 229-240.
Storici, et al., "A 2-mM DNA-Based Marker Recycling System for Multiple Gene Disruption in the Yeast *Saccharomyces cerevisiae*", Yeast, 1999, 15; p. 271-283.
Waghmare, et al., "Specific Targeted Integration of Kanamycin Resistance-Associated Nonselectable DNA in the Genome of the Yeast *Saccharomyces cerevisiae*", Biotechniques, 2003, 34; p. 1024-1028.
Weibezahn, et al, "Novel Insights Into the Mechanism of Chaperone-Assisted Protein Disaggregation", Biol. Chem, 2005, 386; p. 739-744.

* cited by examiner

*Primary Examiner* — Anne Gussow
*Assistant Examiner* — Mindy G Brown
(74) *Attorney, Agent, or Firm* — Fishman & Associates, LLC.

(57) ABSTRACT

The invention provides a yeast strain and a method for making the same. The method has the step of replacing the regulation region upstream of the hsp104 gene in the genome of the yeast, so as to accelerate and prolong the expression span of hsp104 gene and enhance the capability of the yeast to ferment and produce ethanol in a high-temperature environment. The yeast is capable of fermenting glucose at a temperature higher than 42° C. to produce ethanol, or biomass ethanol, wherein the ethanol production ratio based on fermentation of glucose is higher than 97%. Being able to synchronize the degradation/hydrolysis stage and fermentation stage of biomass ethanol producing process, the yeast in accordance with the present invention is able to lower the production cost of biomass ethanol and further raise the productivity with its high ethanol production ratio.

7 Claims, 9 Drawing Sheets

RECOMBINANT THERMOTOLERANT YEAST WITH A SUBSTITUTE HEAT SHOCK PROTEIN 104 PROMOTER

BACKGROUND OF THE INVENTION

1. Field of the Invention

The present invention relates to a novel recombinant yeast substrain, especially to a recombinant yeast substrain suitable for the production of ethanol by fermentation under 42° C. with high efficiency. The recombinant yeast substrain was constructed by replacing the genomic regulatory region for yeast gene hsp104 using linear DNA transformation, so as to alter the behavior of Hsp104 protein under stress and to facilitate the production of alcohol by high-temperature fermentation.

2. Description of the Prior Art

Biomass ethanol is a biomass fuel that generates bio-energy and is obtained by conversion of biomass. Said biomass may be molasses or plants such as maize, wheat or potatoes that allow production of biomass ethanol through the processes of fermentation and distillation. Biomass ethanol is known as a feasible way to reduce dependence on fossil fuels.

Materials for making biomass ethanol are roughly classified into three categories:

1) sugar materials derived from monosaccharide-abundant sugar corps such as sugar cane or sorgo;

2) starch materials derived from wheat or corn; and 3) cellulosic materials derived from agricultural wastes.

Materials of the first and second categories primarily come from food corps. Using such material leads to the zero-sum competition between food and energy applications that are both based on food corps. Materials of the third category, though raise no competition between food and energy applications, require a high production cost yet to be overcome.

The method for making ethanol from the cellulosic materials of the third category may be largely divided into four stages:

1) pretreatment with weak acid, weak base or ammonia-gas explosions to separate cellulose or hemicellulose from the complex comprising binding lignin, so as to facilitate the chemical or biological processing in following stages.

2) degeneration or hydrolysis for obtaining free sugars;

3) fermentation of mixed hexose and pentose to produce ethanol; and 4) collection and distillation of the product for obtaining biomass ethanol.

One of the means for lowering the production cost is to synchronize the degeneration/hydrolysis stage and the fermentation stage.

However, the operation temperature for the cellulose enzyme employed in the degeneration/hydrolysis stage is approximately 45-60° C., which is higher than the fermentation temperatures of most industrial brewing yeasts (*Saccharomyces cerevisiae*). Should a yeast with high-temperature tolerance capable of working under the high temperature of the degeneration/hydrolysis stage be cultivated, such a thermotolerant yeast would synchronously proceed the tasks of the degeneration/hydrolysis stage and the fermentation stage, so as to lower the production cost of biomass ethanol.

Only a few of antecedent technologies are relevant to thermotolerant yeast as below listed works:

Yamada et al. (US patent application publication number: US 2010/0062506), with screening media containing high concentration of sugar and alcohol thermotolerant, have isolated yeast *Kluyveromyces marxianus* capable of producing ethanol by fermentation of sugar cane juice and peaking best productivity as high as 1.51 g of ethanol per liter per hour at 40° C.

Forrester et al. (US patent application publication number: US 2011/0033907) have isolated *Saccharomyces cerevisiae* strains YE1358 and YE1615. At 37° C., fermentation of 250 g/L maize flour and 2 mM $CaCl_2$ with YE1615 gives approximately 130 g/L ethanol.

Abbas et al. (US patent application publication number: US 2009/0155872) have constructed a plasmid comprising 1) *H. polymorpha* (*P. angusta*) glyceraldehyde-3 phosphate dehydrogenase (GADPH) promoter-heat shock protein 104 (hsp104) gene and 2) GADPH promoter-xylulokinase. Transforming *H. polymorpha* with the plasmid suppresses the activity of acid trehalase (ATH1) and raises the capability of *H. polymorpha* to ferment 12% xylose for producing ethanol.

Edgardo et al. (Edgardo et al. 2008, *Enzym. Microb. Tech.* 43, 120-123) have screened *Saccharomyces cerevisiae* at 35-45° C. to isolate strains capable of growing and fermenting glucose at 42° C. However, the fermentation efficiency of the strain is 75% lower than the theoretical value in a solution of 50 g/L glucose concentration at 40° C., and is 25% lower at 52° C.

Benjaphokee et al. (Benjaphokee et al. 2012, *N. Biotechnol.* 29, 379-386), by crossing the spores of thermotolerat *Saccharomyces cerevisiae* HB8-3A and ethanol-productive *Saccharomyces cerevisiae* TISTR5606, have obtained a strain, TJ14, capable of fermenting glucose at 41° C. in a pH 3.5 solution of glucose concentration 100 g/L with a peak fermentation efficiency as high as 90%.

Lindquist and Kim have identified that a molecular chaperone in yeast, the molecular chaperone Hsp104, is capable of separating gathered proteins and refold the same, which raises the thermotolerance of the yeast (Bösl, et al. 2006, *J. Struct. Biol.* 156, 139-148). Hsp104 and Hsp70/40 extract polypeptide chains out from an aggregated protein complex and facilitate the refolding of the same (Lee et al. 2003, *Cell* 115, 229-240; Waghmare et al. 2003, *Biotechniques* 34, 1024-1028; Storici et al. 1999, *Yeast* 15, 271-283; Weibezahn et al. 2005, *Biol. Chem.* 386, 739-744). Heat shock protein and other molecular chaperones are indispensable for cellular stasis of a cell. In normal circumstances, it is vital that these chaperones are sufficiently expressed. When under environmental stress, misfolded proteins accumulate and disrupt cellular physiological conditions. Misfolded proteins may further induce generation of chaperones, which help restore and maintain normal cellular physiological conditions. Comparing with other chaperones, Hsp104 is insignificant under normal conditions and thus its low concentration. However, under fatal environmental stress, the concentration of Hsp104 acutely rises in a short period of time to restore the activities of the disabled proteins accumulated in the cell. In *Saccharomyces cerevisiae*, Hsp104, though expression level of which raises responsive to a stress, the expression level lowers in a few hours, which fails to allow *Saccharomyces cerevisiae* to survive at high temperature for a significantly long period of time and thus makes *Saccharomyces cerevisiae* unsuitable for synchronized hydrolysis and fermentation.

Altered expression of recombinant genes to enhance tolerance of yeasts to stress is practicable. However, few available recombination tags tend to be insufficient. In order to reuse the recombination tags that are few in number, the FLP/FRT recognition-site-specific recombination system is employed. The natural flippase recombinase gene, flp, is derived from the 2 μm plasmid of *Saccharomyces cerevisiae*; FRT stands for "Flippase recombinase Recognition Target." The FRT comprises 34 base pairs (bp/bps): SEQ ID NO: 12, and is divided into two regions. The first consecutive 13 bps and last 13 consecutive bps belong to a complementary region, which is the FLP recognition site. The central 8 bps are named as the core region, which is asymmetric. FLP recognizes two identical FRT in the same direction and flip-out the gene flanked by the two FRT to accomplish specific gene recombination. The possibility of the occurrence of recombination based on two non-identical FRTs is extreme low (Storici et al. 1999, *Yeast* 15, 271-283).

Due to the lack of thermotolerant *Saccharomyces cerevisiae* having glucose fermentation efficiency higher than 95% and method for making same, it is apparent that there is a present need for such means to lower the production cost of cellulosic biomass ethanol.

To overcome the shortcomings that the prior art fails to provide a thermotolerant yeast and fails to lower the production cost for biomass ethanol, the present invention provides a thermotolerant yeast with a substitute heat shock protein 104 promoter to mitigate or obviate the aforementioned problems.

SUMMARY OF THE INVENTION

The main objective of the invention is to provide a new recombinant *Saccharomyces cerevisiae* having an ethanol production ratio higher than 95% based on fermentation of glucose at a temperature higher than 42° C.

The method for making the yeast in accordance with the present invention comprises the step of replacing the regulation region upstream of the hsp104 gene in the genome of the yeast, so as to accelerate and prolong the expression span of hsp104 gene and enhance the capability of the yeast to ferment and produce ethanol in a high-temperature environment.

The yeast in accordance with the present invention has been deposited in China Center for Type Culture Collection (CCTCC) on Jun. 28, 2012, confirmed viable on Jul. 5, 2012, and assigned a deposit designation "CCTCC M 2012254," which is a recombinant yeast substrain derived from the *Saccharomyces cerevisiae* strain sake yeast Kyokai 6. CCTCC is an International Depository Authority (IDA) under the provisions of the Budapest Treaty having a place of business at Wuhan University, Wuhan 430072 P. R. China, in accordance with the statement of which that the deposit, CCTCC M 2012254, will be made available if a patent office signatory to the Budapest Treaty certifies one's right to receive and will be maintained for a period of at least 30 years after the date of deposit, and for a period of at least five years after the most recent request for a sample.

The deposited yeast deposited as deposit CCTCC M 2012254 in CCTCC is capable of fermenting glucose at a temperature higher than 42° C. to produce ethanol, or biomass ethanol, wherein the ethanol production ratio based on fermentation of glucose is higher than 97%. Being able to synchronize the degradation/hydrolysis stage and fermentation stage of biomass ethanol producing process, the yeast in accordance with the present invention is able to lower the production cost of biomass ethanol and further raise the productivity with its high ethanol production ratio.

Other objectives, advantages and novel features of the invention will become more apparent from the following detailed description when taken in conjunction with the accompanying drawings.

DETAILED DESCRIPTION OF THE PREFERRED EMBODIMENTS

An embodying of the present invention first involves in constructing a specific targeted integration of kanamycin resistance-associated non-selectable DNA promoter exchange platform, which employs linear DNA transformation to replace the upstream regulation region of hsp104 gene in yeast genome, so as to accelerate and prolong the expression span of hsp104 gene and enhance the capability of the yeast to ferment and produce ethanol at a high-temperature.

Figure 1:
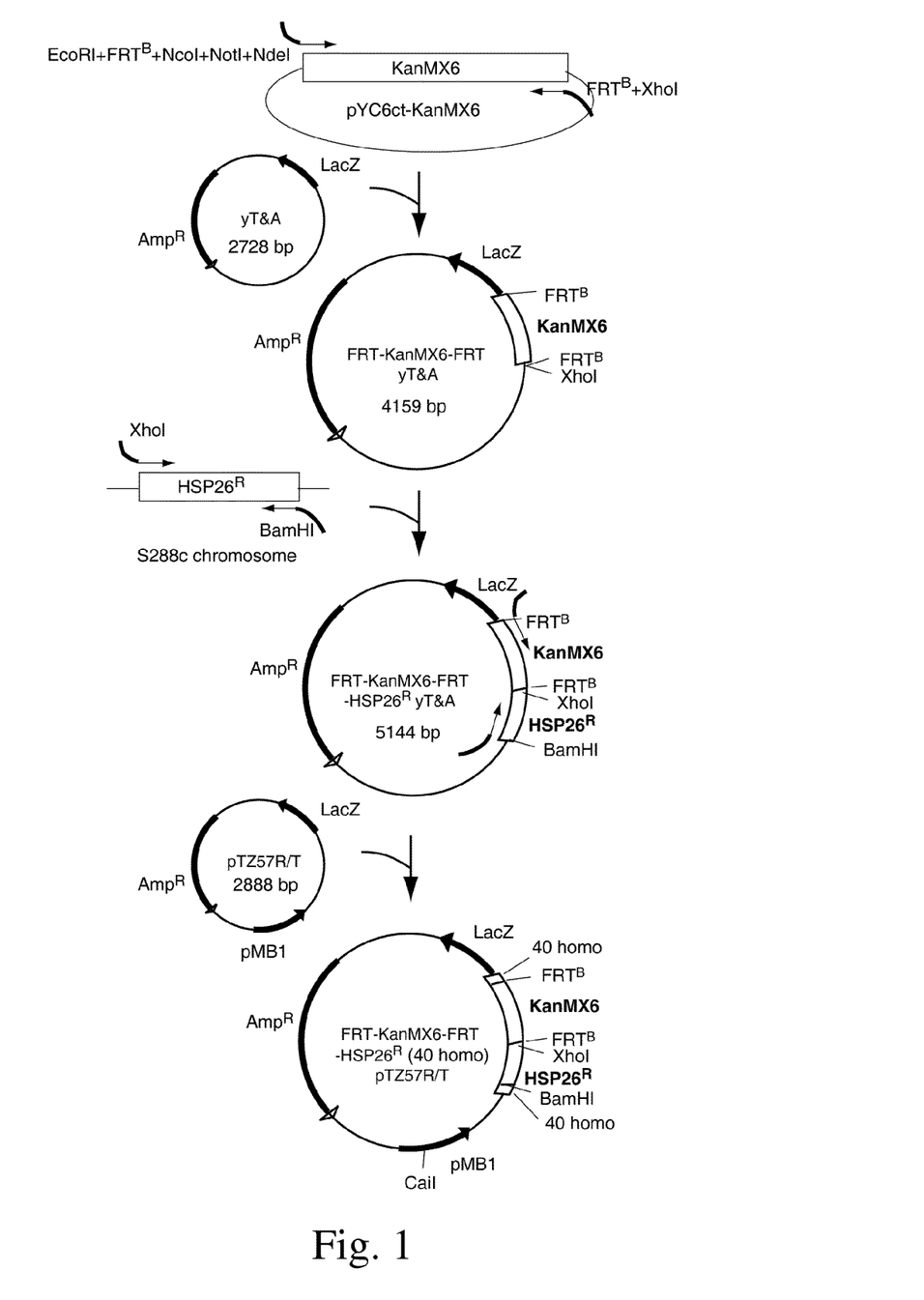
FIG. 1 is a schematic drawing of the construction of plasmid $FRT^B$-KanMX6-$FRT^B$-HSP26$^R$ (40 homo) pTZ57R/T for a yeast genome exchange platform.

As shown in FIG. 1, the construction of plasmid pTZ57R/T for a yeast genome exchange platform using $FRT^B$-KanMX6-$FRT^B$-HSP26$^R$ (40 homo) employs antibiotic resistance gene KanMX6 with a sequence as shown in SEQ ID NO: 9 and uses plasmid pYC6ct-KanMX6 and the chromosome of *Saccharomyces cerevisiae* strain s288c as PCR templates accompanying SEQ ID NOs: 1-7 as primers.

SEQ ID NO: 1 is a forward primer for KanMX6 and SEQ ID NO: 2 is a backward primer for KanMX6, while SEQ ID NO: 3 is a forward primer for hsp26 and SEQ ID NO: 4 is a backward primer for hsp26. A sequence having KanMX6 for resistance against kanamycin, a fragment containing KanMX6 and the regulation region of hsp26 flanked by two FRT sequences is obtained by using the two of the aforementioned primer pairs. The sequence of KanMX6 is first integrated into vector yT&A and the regulation region of hsp26 (HSP26$^R$) digested with XhoI and BamHI is subsequently integrated to the yT&A vector. The plasmid so constructed is named as FRT-KanMX6-FRT-HSP26$^R$ yT&A.

In order to lower the rate of homologous recombination between designed plasmid and the FRT sequence of the yeast 2 μm plasmid, a fragment containing KanMX6 flanked by FRT having mutated FRT core regions is obtained by using SEQ ID NO: 5 as the forward primer for FRT$^B$ and SEQ ID NO: 6 as the backward primer for FRT$^B$. The fragment containing KanMX6 is first integrated into vector yT&A and the regulation region of hsp26 (HSP26$^R$) digested with XhoI and BamHI is subsequently integrated to the yT&A vector. The plasmid constructed as aforementioned is named as FRT$^B$-KanMX6-FRT$^B$-HSP26$^R$ yT&A.

The FRT$^B$-KanMX6-FRT$^B$-HSP26$^R$ fragment is further manipulated as being flanked by two homologous sequences (40 homo) in order to exchange with the upstream regulation region of hsp104 gene.

FRT$^B$-KanMX6-FRT$^B$-HSP26$^R$ yT&A is then cleaved by BamHI to be linear DNA. SEQ ID NO: 7 is a forward primer for adding a homologous sequence and SEQ ID NO: 8 is a backward primer for adding another homologous sequence, both homologous sequences, though of different sequences, are 40 bps in length and abbreviated "40 homo." PCR with the primer pair, SEQ ID NOs: 7 and 8, gives a DNA fragment that is further integrated into a TA-cloning vector pTZ57R/T. The plasmid constructed with the foregoing process is named as FRT$^B$-KanMX6-FRT$^B$-HSP26$^R$ (40 homo) pTZ57R/T.

Before transformating a yeast strain of Saccharomyces cerevisiae Kyokai strain series with plasmid FRT$^B$-KanMX6-FRT$^B$-HSP26$^R$ (40 homo) pTZ57R/T with, e.g., lithium acetate, the plasmid is first cleaved with Cail to be linear DNA. The linear DNA made from the plasmid is used to transform Saccharomyces cerevisiae strains Kyokai 6 and s288C. The colonies with successfully replaced DNA, i.e., Saccharomyces cerevisiae substrains of which upstream regulation region of hsp104 has been replaced with the FRT$^B$-KanMX6-FRT$^B$-HSP26$^R$ fragment, are confirmed by colony PCR. The Saccharomyces cerevisiae substrain, which is derived from the Kyokai 6 strain, having sequences successfully replaced with a PCR primer pair designed based on the peripheral sequence of the replaced DNA fragment, i.e., SEQ ID NOs: 10 and 11, is named as Kyokai 6-HSP104$^R$/26$^R$ Kan.

The thermotolerance of Kyokai 6-HSP104$^R$/26$^R$ Kan is tested using spot assay. Being incubated in yeast peptone dextrose agar plate (YPD agar plate) at 30 to 46° C. for 16 hours, Kyokai 6-HSP104$^R$/26$^R$ Kan demonstrates superior thermotolerance than Kyokai 6 from which it is originated. When shake flask fermenting at 42° C. in an YPD medium, Kyokai 6-HSP104$^R$/26$^R$ Kan reaches a saturated cell density in 7 hours, which indicates a faster growth rate than Kyokai 6. In addition, only at the 8-hour time point does Kyokai 6-HSP104$^R$/26$^R$ Kan give trace ethanol, which may be attributed to the leak-in of oxygen to the shake flask when sampling and the consumption of ethanol by Kyokai 6-HSP104$^R$/26$^R$ Kan that performs respiration at a higher rate. When fermented with fermenter in 5 L of YPD at 42° C., Kyokai 6-HSP104$^R$/26$^R$ Kan grows faster than Kyokai 6. Kyokai 6-HSP104$^R$/26$^R$ Kan consumes 80 g/L glucose in 14 hours and produce ethanol based on glucose at an ethanol production ratio of 97%.

EXAMPLE 1

The instant example demonstrates the preparation and purification of plasmids. A feasible embodiment has been carried out as follows:

2 mL of LB medium supplied with 100 ng/mL of ampicillin containing ECOS™ 101 (Yeastern, E. coli DH5α) transformed with plasmid pYC6ct-KanMX6 cultivated at 37° C. under 175 rpm shaking for 12 hours was added in 1.75-mL microcentrifuge tubes to be centrifuged for 1 minutes at 14000 rcf. The supernatant was removed leaving bacteria pellet, which was then repetitively pipetted and resuspended with 200 μL of MiniPrep-V$^2$ solution II. The suspension was stood for 5 minutes and then repetitively pipetted and resuspended with 300 μL of MiniPrep-V$^2$ solution III, after which centrifugation at 14000 rcf for 5 minutes was performed.

700 μL of supernatant was collected in spin columns (collection tubes) and centrifuged for 30 seconds. The liquid in the spin columns was removed and 700 μL of wash solution was added. An additional 30-second centrifugation was performed and the wash solution was removed. The spin columns were centrifuged for 3 minutes and respectively placed in 1.75 mL microcentrifuge tubes with their lids left open. The open spin columns were dried at 60° C. for 20-30 minutes, after which 55 μL of Elution solution was added and the spin columns were centrifuged for 2 minutes. The solution in the spin columns now contained the purified plasmid. 1 μL of the solution were used for measuring the concentration and purity of the plasmid with Nano Drop® 1000.

EXAMPLE 2

The instant example demonstrates purification of chromosome of Saccharomyces cerevisiae. One feasible embodiment has been performed as follows:

1.5 mL of YPD medium containing Saccharomyces cerevisiae cultivated at 30° C. under 200 rpm shaking for 16 hours was added into a 1.75-mL microcentrifuge tube and centrifuged at 12000 rpm for 1 minute. The supernatant was removed and 300 μL of Master Pure™ Lysis solution was used to resuspend the yeast. The suspension was allowed to react at 65° C. for 15 minutes, followed by a 5-minute ice bath. The tube was supplied with 150 μL of Master Pure™ MPC solution (Protech) and was shaked by a tube-shaker for 10 seconds, after which a centrifugation at 12000 rpm was performed for 10 minutes. 500 μL of supernatant was taken to a new 1.75-mL microcentrifuge tube and mixed with 500 μL of isopropanol by repetitive inversion, the mixture of which was than centrifuged at 12000 rpm for 10 minutes. The supernatant was removed and a washing with 500 μL of 70% alcohol was performed prior to a short centrifugation. The washing alcohol was removed and 35 μL of TE buffer (pH 8) was used to dissolve the DNA. The DNA solution was than stored at −20° C.

EXAMPLE 3

The instant example demonstrates the construction of plasmid FRT-KanMX6-FRT yT&A. One feasible embodiment has been performed as follows:

A PCR program setting forth an initial denaturation at temperature 95° C. for 7 minutes, 30 cycles and a final extension for 10 minutes was employed in the instant embodiment. Each of the cycles has a denaturation step at 95° C. for 1 minute, an annealing step at 70° C. for 1 minute and an extention step at 72° C. for 1.7 minute. Plasmid pYC6ct-KanMX6 was used as the PCR template and SEQ ID NOs: 1 and 2 were used as forward and backward primers.

Figure 2:
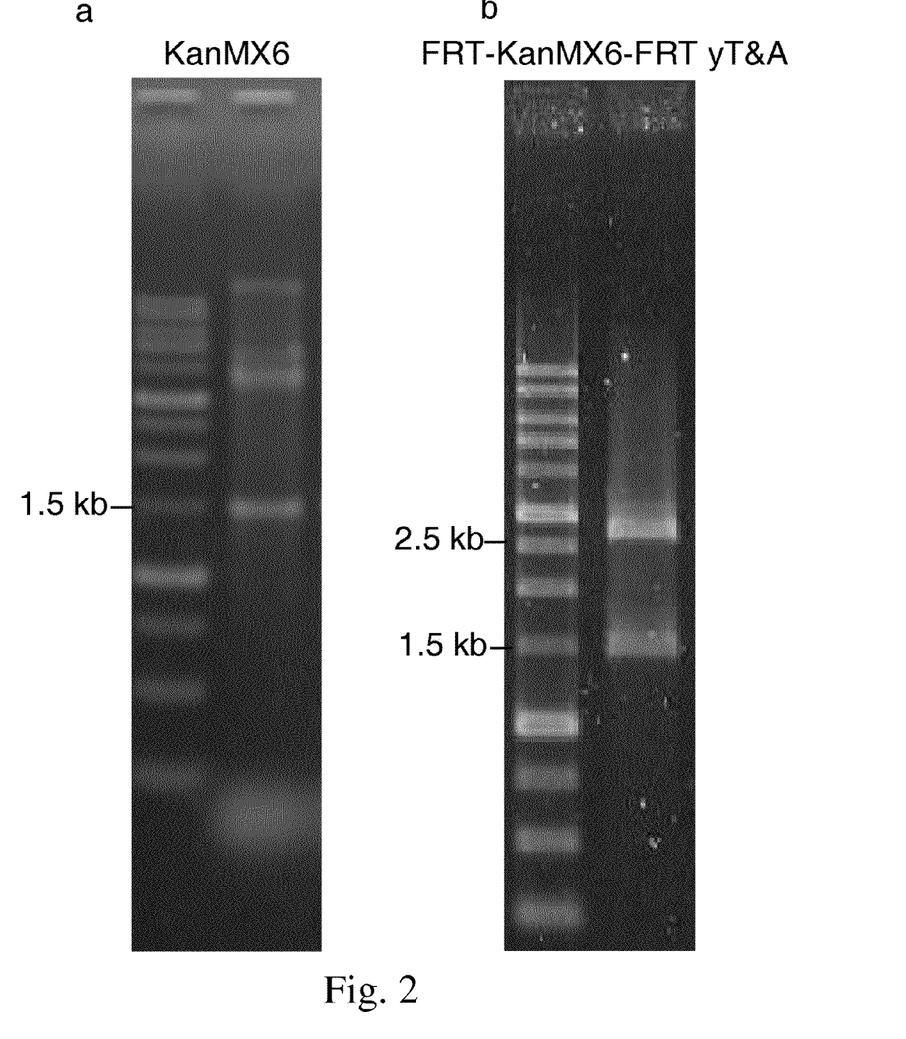
FIG. 2a is an image of an electrophoresis result of a PCR product FRT-KanMX6-FRT, i.e., a fragment containing KanMX6 flanking by two FRTs, sizing 1431 bps.
FIG. 2b is an image of an electrophoresis result of DNA fragments obtained by cleaving FRT-KanMX6-FRT yT&A with EcoRI and XhoI, which respectively sizing 2726 bps and 1433 bps.

As shown in FIG. 2a, a sequence, 1431-bps in length, containing a KanMX6 gene for resistance against kanamycin and two FRT sequences flanking the KanMX6 gene was obtained. The sequence was confirmed with voltage-fixed electrophoresis using a 1% argarose gel at 100 V and 50 mA for 50 minutes.

The DNA fragment of the DNA sequence containing the KanMX6 gene was cutted off and purified from the agarose gel using QIAquick Gel Extraction Kit (Qiagen). 100 ng of the DNA fragment was mixed with 2 μL of yT&A vector (Yeastern), 2 μL of Ligation buffer, 0.2 μL of T4 DNA ligase and DI water filling up the total volume to 20 μL. The DNA mixture was allowed to react for 1 hour and deactivated at 70° C. for 5 minutes. 10 μL of the deactivated DNA mixture was added to a ⅓ filled tube of ECOS™ 101 competent cells, followed by 30 minutes of ice bath, 45-90 seconds of 42° C. water bath and another 5-minute ice bath. 200 μL of LB broth was added to the competent cells, which was then spread on a LB agarose plate containing 100 μg/mL of ampicillin and incubated at 37° C. overnight. Yeast strains were so cultivated. As shown in FIG. 2b, the plasmids of the strains were purified and screened with 1% agarose gel electrophoresis to select substrains having the plasmid containing the FRT-KanMX6-FRT yT&A fragment. The plasmids of selected sub strains were sequenced and further confirmed.

EXAMPLE 4

Figure 3:
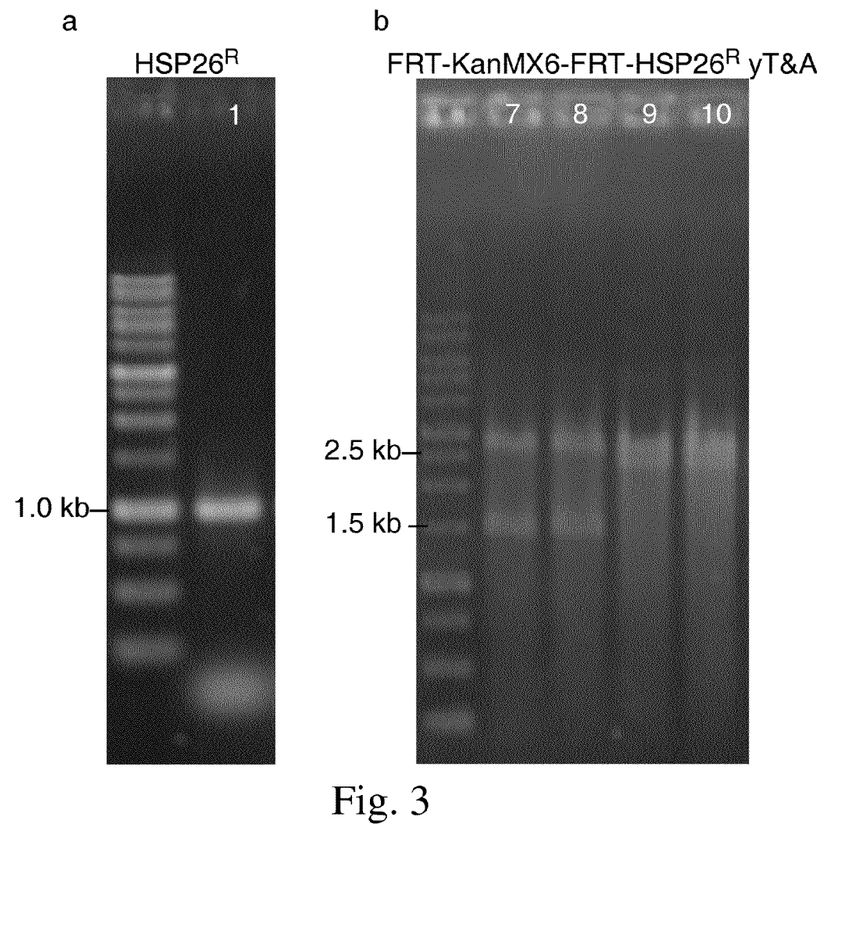
FIG. 3a is an image of an electrophoresis result of a PCR product HSP26$^R$ sizing 985 bps.
FIG. 3b is an image of an electrophoresis result of DNA fragments obtained by cleaving FRT-KanMX6-FRT-HSP26$^R$ yT&A with EcoRI and BamHI, which respectively sizing 2709 bps and 2416 bps.

The instant example demonstrates the construction of plasmid FRT-KanMX6-FRT-HSP26$^R$ yT&A. One feasible embodiment has been performed as follows:

As shown in FIG. 3a, a PCR program setting forth an initial denaturation at temperature 95° C. for 7 minutes, 30 cycles and a final extension for 10 minutes was employed in the instant embodiment. Each of the cycles has a denaturation step at 95° C. for 1 minute, an annealing step at 52° C. for 1 minute and an extention step at 72° C. for 1.7 minute. The chromosome of *Saccharomyces cerevisiae* strain s288c was used as the PCR template and SEQ ID NOs: 3 and 4 were used as forward and backward primers. The PCR product was a 985-bp DNA fragment containing HSP26$^R$.

As shown in FIG. 3b, a mixture of 25 μL of the PCR product, 3 μL of restriction enzyme buffer and 20 μL of XhoI and BamHI restriction enzymes was allowed to react at 37° C. for 2 hours followed by deactivation at 80 or 65° C. for 20 minutes and electrophoresis using 1% agarose gel for purifying a XhoI and BamHI-digested DNA fragment of the sequence containing HSP26$^R$ as aforementioned, which was then ligated to XhoI and BamHI-digested plasmid FRT-KanMX6-FRT yT&A, in order to construct FRT-KanMX6-FRT-HSP26$^R$ yT&A. The resulting plasmid FRT-KanMX6-FRT-HSP26$^R$ yT&A was submitted to sequencing for further confirmation.

EXAMPLE 5

Figure 4:
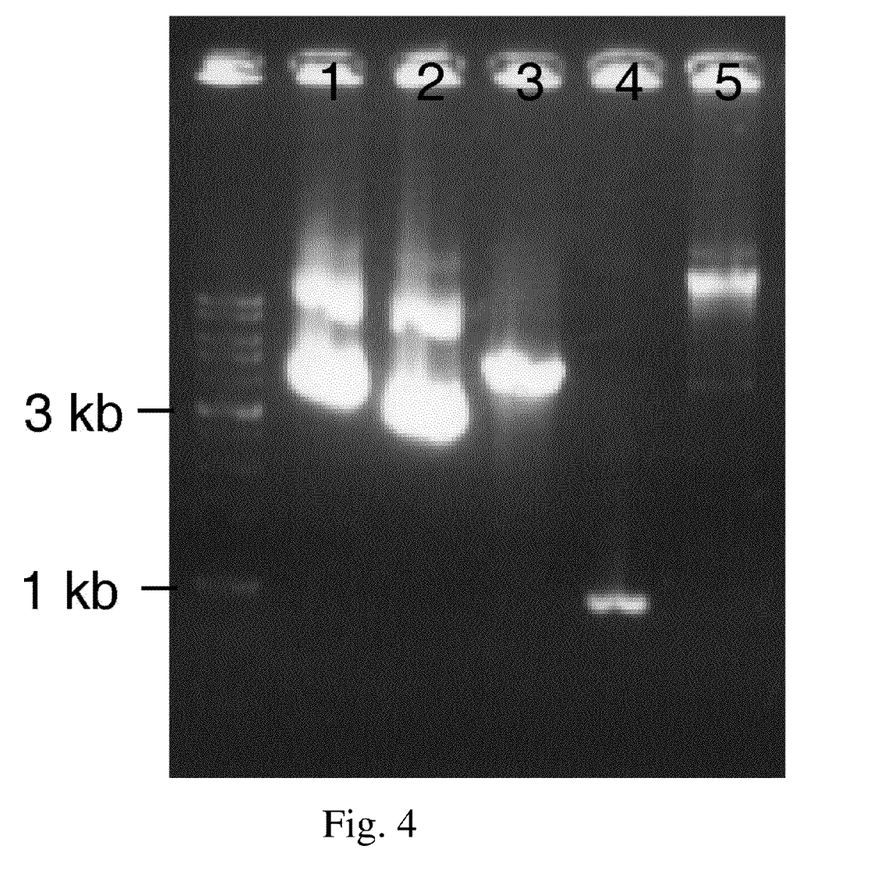
FIG. 4 is an image of an electrophoresis result that in lanes 1 to 5 of which are: 1) plasmid FRT-KanMX6-FRT-HSP26$^R$ yT&A, 2) plasmid $FRT^B$-KanMX6-$FRT^B$-HSP26$^R$, 3) a linear DNA fragment obtained from XhoI and BamHI digested plasmid $FRT^B$-KanMX6-$FRT^B$ yT&A, 4) a fragment cleaved from plasmid FRT-KanMX6-FRT-HSP26$^R$ yT&A by XhoI and BamHI digestion, 5) plasmid $FRT^B$-KanMX6-$FRT^B$-HSP26$^R$ yT&A obtained from ligation of the fragments as in lane 3 and lane 4.

The instant example demonstrates the construction of plasmid FRT$^B$-KanMX6-FRT$^B$-HSP26$^R$ yT&A. One feasible embodiment has been performed as follows:

As shown in FIG. 4, a PCR program setting forth an initial denaturation at temperature 95° C. for 7 minutes and 33 cycles was employed in the instant embodiment. Each of the cycles has a denaturation step at 95° C. for 1 minute, an annealing step at 70° C. for 1 minute and an extention step at 72° C. for 1.7 minute. A linear DNA made from cleaving plasmid FRT-KanMX6-FRT-HSP26$^R$ yT&A with BamHI was used as the PCR template and SEQ ID NOs: 5 and 6 were used as forward and backward primers. The PCR product was a sequence, 1451-bps in length, containing a KanMX6 gene for resistance against kanamycin and two FRT$^B$ sequences flanking the KanMX6 gene was obtained. A DNA fragment of the aforementioned sequence was isolated on and purified from a 1% agarose gel using electrophoresis and QIAquick Gel Extraction Kit (Qiagen).

100 ng of the DNA fragment was mixed with 2 μL of yT&A vector (Yeastern), 2 μL of Ligation buffer, 0.2 μL of T4 DNA ligase and DI water filling up the total volume to 20 μL, allowed to react at 22° C. for 1 hour and then deactivated at 70° C. for 5 minutes. 10 μL of the deactivated DNA mixture was added into a ⅓ filled tube of competent cell ECOS™ 101, followed by 30 minutes of ice bath, 45-90 seconds of 42° C. water bath and another 5-minute ice bath. 200 μL of LB broth was added to the competent cells, which was then spread on a LB agarose plate containing 100 μg/mL of ampicillin and incubated at 37° C. overnight. Yeast strains were so cultivated. The plasmids of the strains were purified and screened with 1% agarose gel electrophoresis to select substrains having the plasmid containing the FRT$^B$-KanMX6-FRT$^B$ yT&A fragment.

The XhoI-BamHI fragment of plasmid FRT-KanMX6-FRT-HSP26$^R$ yT&A containing HSP26$^R$ was cleaved off with the restriction enzymes and integrated into the plasmid FRT$^B$-KanMX6-FRT$^R$ yT&A to obtain plasmid FRT$^R$-KanMX6-FRT$^R$-HSP26$^R$ yT&A.

EXAMPLE 6

Figure 5:
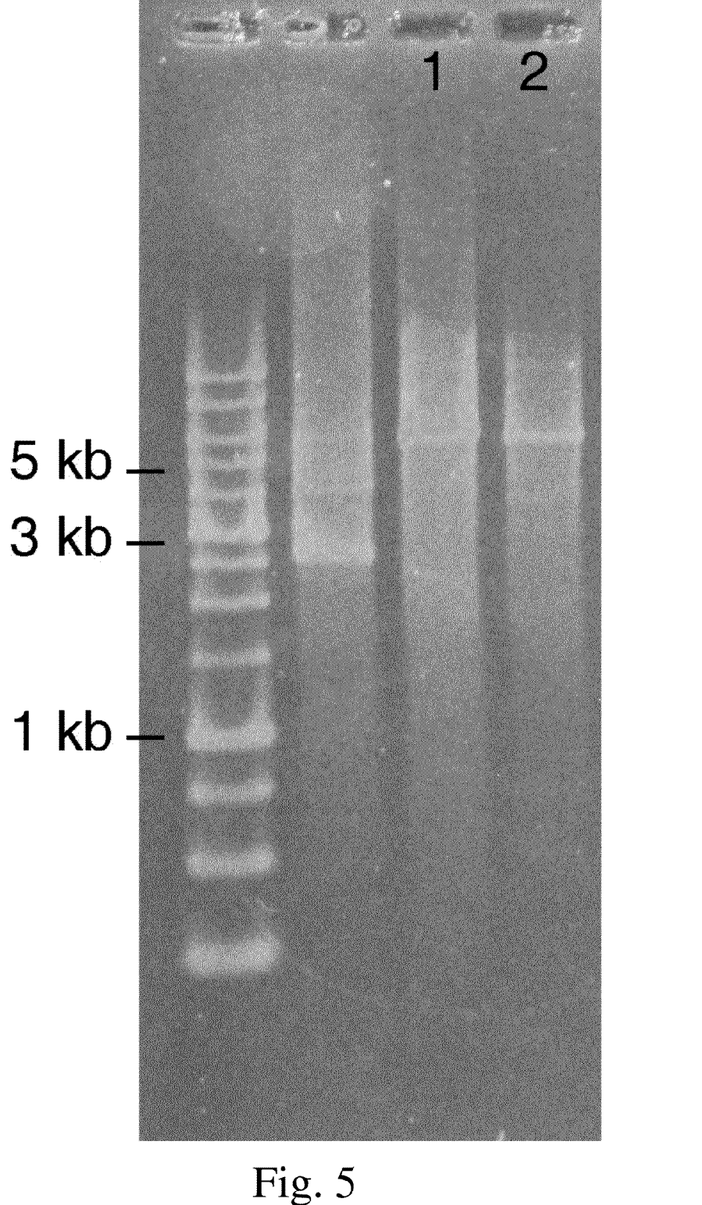
FIG. 5 is an image of an electrophoresis result that lanes 1 and 2 are loaded with linear DNA fragments obtained from BamHI digested plasmid $FRT^B$-KanMX6-$FRT^B$-HSP26$^R$ (40 homo) pTZ57R/T.

The instant example demonstrates the construction of plasmid FRT$^R$-KanMX6-FRT$^R$-HSP26$^R$ (40 homo) pTZ57R/T. One feasible embodiment has been performed as follows:

As shown in FIG. 5, a PCR program setting forth an initial denaturation at temperature 95° C. for 3 minutes, 30 cycles and a final extension for 30 minutes was employed in the instant embodiment. Each of the cycles has a denaturation step at 95° C. for 1 minute, an annealing step at 66.8° C. for 2 minutes and an extention step at 72.5° C. for 3 minutes. A linear DNA made from plasmid FRT$^R$-KanMX6-FRT$^R$-HSP26$^R$ yT&A with BamHI digestion was used as the PCR template and SEQ ID NOs: 7 and 8 were used as forward and backward primers, wherein the first 40 bps of SEQ ID NOs: 7 and 8 are respectively homologous sequences to the upstream regulation region of hsp104 gene, for synthesizing two 40-bp homologous sequences (40 homo) flanking the FRT$^R$-KanMX6-FRT$^R$-HSP26$^R$ fragment, so as to exchange with the upstream regulation region of hsp104 gene. The resulting DNA fragment was integrated into a TA-cloning vector pTZ57R/T to constitute plasmid FRT$^R$-KanMX6-FRT$^R$-HSP26$^R$ (40 homo) pTZ57R/T then used for transforming ECOS™ Blue (Yeastern, *E. coli* XL-1 blue).

EXAMPLE 7

The instant example demonstrates the transformation of yeast with plasmid FRT$^B$-KanMX6-FRT$^B$-HSP26$^R$ (40 homo) pTZ57R/T. One feasible embodiment has been performed by lithium acetate transformation of yeast as follows:

Yeasts were pre-incubated for 12 hours and the yeast-density of the suspension was adjusted that the OD$_{600}$ was from 2 to 4, after which the incubated suspension was diluted that OD$_{600}$ was from 0.2 to 0.4. The suspension was further incubated for 3 hours while maintaining its OD$_{600}$ to be less than 0.6. The suspension was then centrifuged at 4° C. and 12000 rpm for 5 minutes. The supernatant was removed and 25 mL of sterilized deionized water was added to resuspend the yeast pellet. The suspension was centrifuged at 4° C. for 5 minutes at 12000 rpm. The supernant was removed and the yeast pellet was left. 0.3 mL of TE/LiAc (10 mM Tris; 10 mM EDTA, 0.1 M LiAc, pH 7.5) was added and yeast competent cells were prepared.

In one 1.75-mL microcentrifuge tube, more than 0.1 μg of a linear DNA made from CalI digested $FRT^B$-KanMX6-$FRT^B$-$HSP26^R$ (40 homo) pTZ57R/T, and 0.1 mg of carrier DNA (sheared, denatured herring testes DNA) was added and mixed 0.1 mL of yeast competent cells were further added, immediate followed by addition of 0.6 mL of PEG/LiAc (10 mM Tris; 10 mM EDTA, 0.1 M LiAc, 40% PEG4000, pH 7.5). The microcentriguge tube was shaked with a tube shaker for 10 seconds allowing well mixing of the aforementioned intgredients, and then incubated in a constant-temperature incubator at 30° C. and being shaked at 200 rpm for 30 minutes. 70 μL DMSO was then added and mixed by repetitive inversions. A 42° C. heat shock with a duration of 15 minutes was immediately performed. A 5-minute ice bath followed. 1 mL of YP medium was added. After a 3-hour incubation at 30° C. shaking at 200 rpm, 200 μL of the incubated suspension was spread on a YPD G418 solid medium for screening.

EXAMPLE 8

The instant example demonstrates the screening of yeast substrains with yeast colony PCR. One feasible embodiment has been performed as follows:

Yeast colony PCR was performed using Yeast Protein Kit™ (Zymo Research). 20 μL of Y-Lysis Buffer and 1 μL of Zymolyase solution were added in a 1-mL microcentrifuge tube. Trace yeast from a colony on the aforementioned solid medium was transferred in to the mixture in the microcentrifuge tube and was incubated at 37° C. for 1 hour. 2 μL of the incubated suspension was used for PCR.

Figure 6:
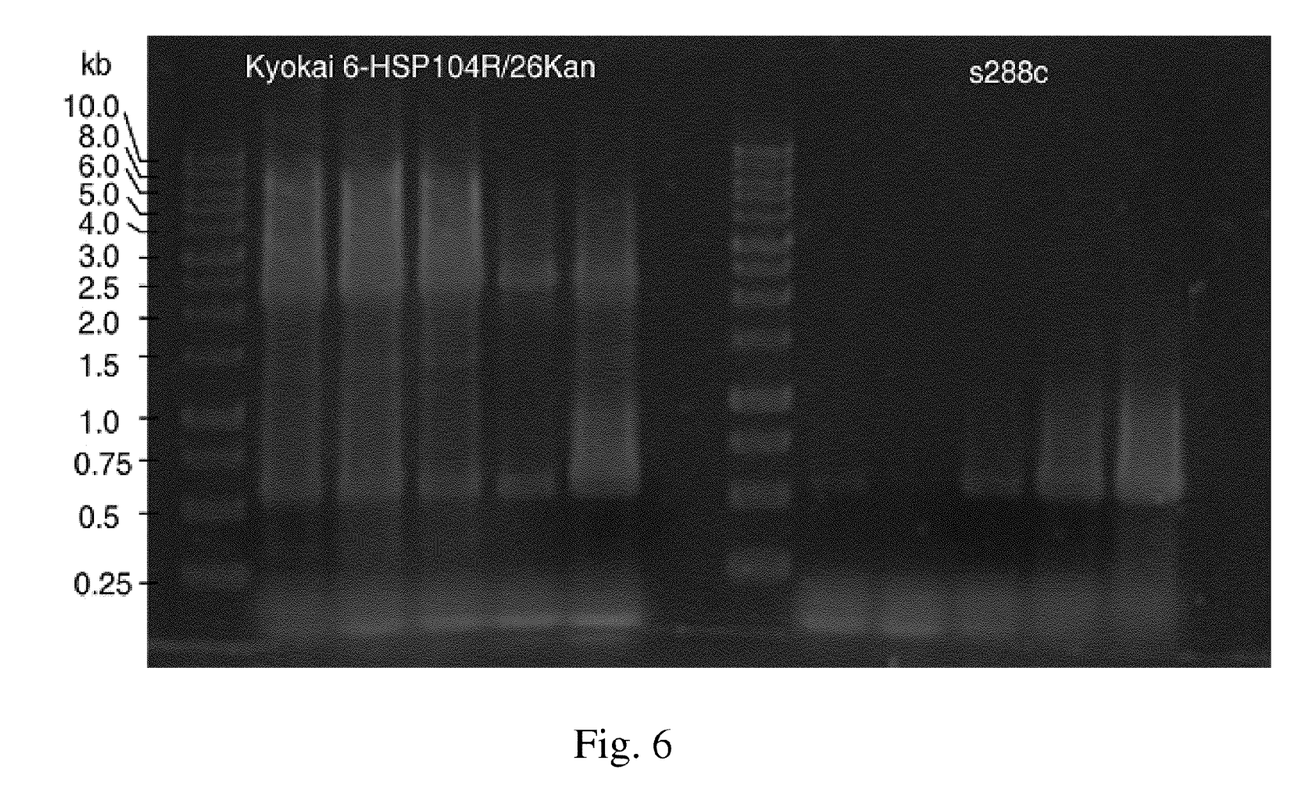
FIG. 6 is an image of an electrophoresis result of colony PCR products of Kyokai 6-HSP104$^R$/26$^R$ Kan and s288c yeast.

As shown in FIG. 6, the substrain derived from Kyokai 6 strain whose DNA was successfully replaced represented a PCR product being a 2.5 kb DNA fragment. The substrain was named Kyokai 6-$HSP104^R/26^R$ Kan, based on which a deposit, CCTCC M 2012254, has been made in an IDA, i.e., CCTCC.

EXAMPLE 9

The instant example demonstrates the thermotolerance spot assay for yeast.

Figure 7:
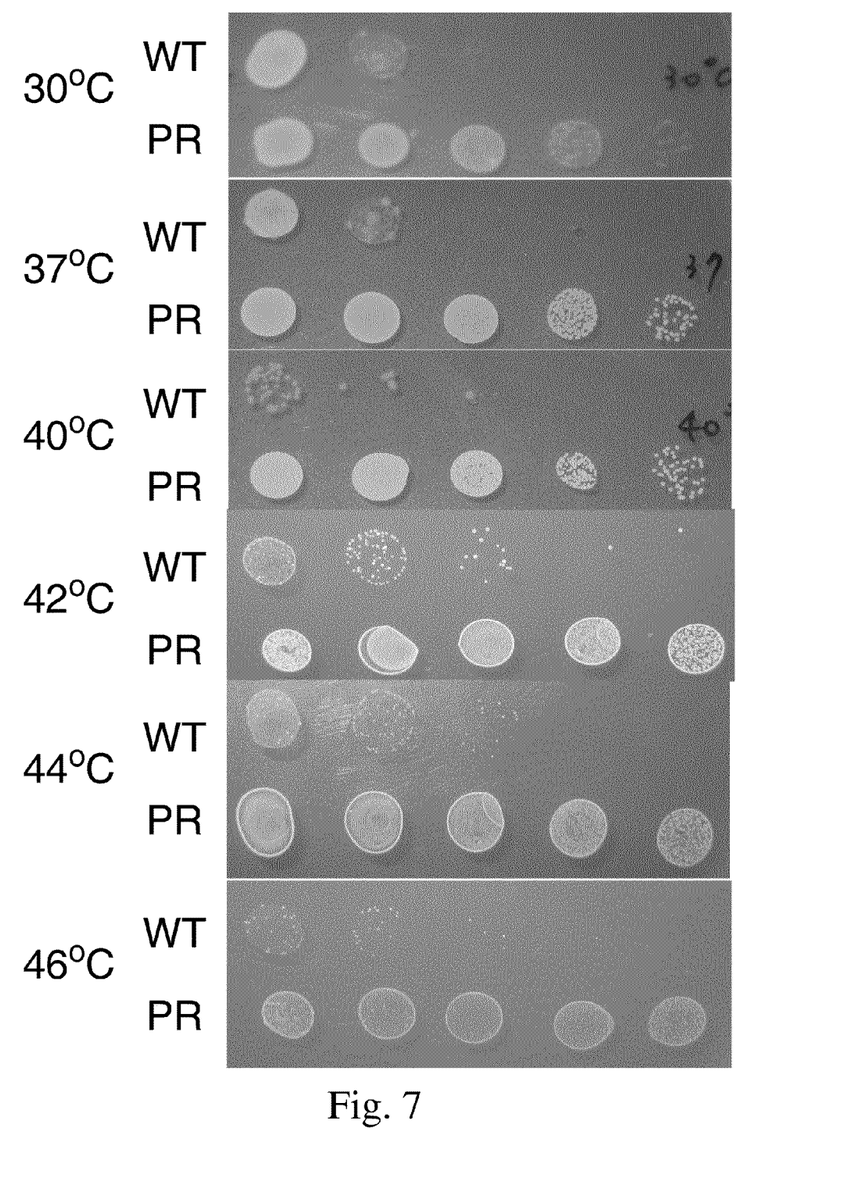
FIG. 7 is an image of a thermotolerance spot assay wherein "WT" represents Kyokai 6 and "PR" represents Kyokai 6-HSP104$^R$/26$^R$ Kan.

Yeast substrain Kyokai 6-$HSP104^R/26^R$ Kan was picked with a toothpick into 1.5 mL of YPD medium and cultivated submerged. When $OD_{600}$ value of the suspension became 2 to 4, the suspension was 10-fold diluted and re-activated. 3 hours later, $OD_{600}$ value was further measured and adjusted to 0.3 with YP medium. A suspension so adjusted was defined a 1× suspension. 100 μL of 1× suspension was 10-fold diluted and defined as a $10^{-1}$× suspension. With similar methods, $10^{-2}$×, $10^{-3}$× and $10^{-4}$× suspensions were made. 10-μL aliquots of the aforementioned suspensions of different concentrations was serially dropped on YPD solid mediums and respectively incubated at 30° C., 37° C., 40° C., 42° C., 44° C. and 46° C. for 16 hours. As shown in FIG. 7, Kyokai 6-$HSP104^R/26^R$ Kan demonstrated superior thermotolerance than the Kyokai 6 strain from which it is derived from.

EXAMPLE 10

The instant example demonstrates the shake flask fermentation experiment at 42° C.

With a toothpick or similar tool, trace Kyokai 6-$HSP104^R/26^R$ Kan was taken to 5 mL of YPD medium to perform submerged cultivation. When the $OD_{600}$ value of the cultivation medium had been higher than 7, the cultivation medium was diluted 10-fold diluted and re-activated for 3 hours. The $OD_{600}$ value was measured again and the cultivation medium was adjusted with YPD medium that the glucose concentration was 80 g/L and the OD value was 0.3. Shake flask fermentation was performed at 42° C. At every 1-hour interval, two 1-mL samples were taken from the fermentation suspension. One of the 1-mL sample of each time point was used for OD values measurement. The other 1-mL sample of each time point was centrifuged at 13000 rpm, from which supernatant was collected and filtered through a 0.22 μm filter, so as to measure the glucose concentration and ethanol concentration with HPLC.

Figure 8:
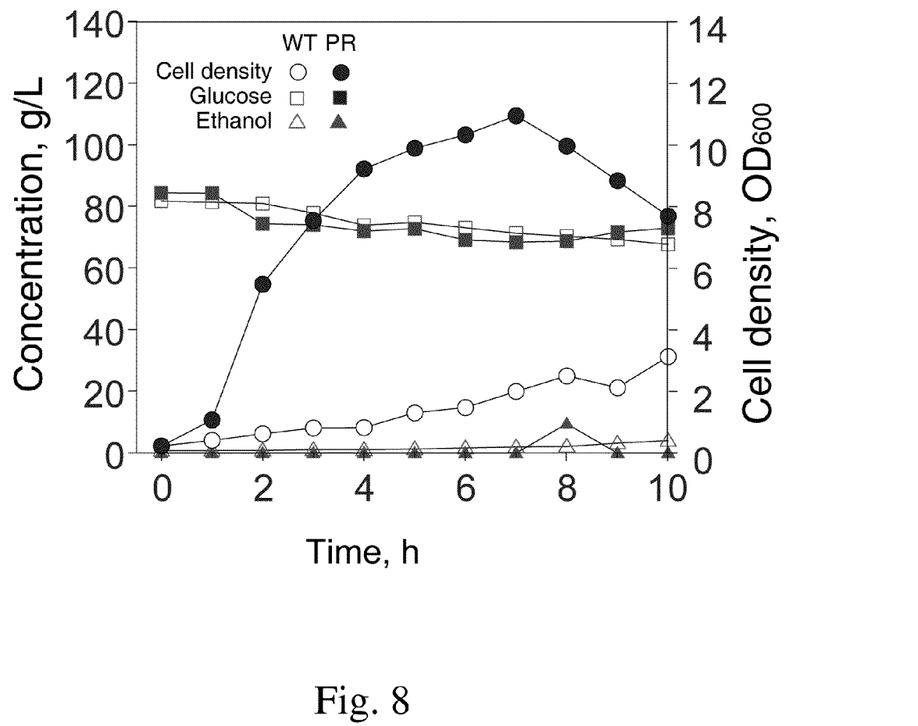
FIG. 8 is a chart of the result of a shake flask fermentation experiment wherein "WT" represents Kyokai 6 and "PR" represents Kyokai 6-HSP104$^R$/26$^R$ Kan.

As shown in FIG. 8, when performing shake flask fermenting at 42° C. in an YPD medium, Kyokai 6-$HSP104^R/26^R$ Kan reached a saturated cell density in 7 hours, which indicated a faster growth rate than Kyokai 6. In addition, only at the 8-hour time point did Kyokai 6-$HSP104^R/26^R$ Kan give trace ethanol, which may be attributed to the leak-in of oxygen into the shake flask when sampling and the consumption of ethanol by Kyokai 6-$HSP104^R/26^R$ Kan that performs respiration at a higher rate.

EXAMPLE 11

The instant example demonstrates the fermentation experiment using fermenters at 42° C.

With a toothpick or similar tool, Kyokai 6-$HSP104^R/26^R$ Kan that had grown to a rod or string shape was submitted to 100 mL of YPD medium to perform submerged cultivation. When the $OD_{600}$ value of the cultivation medium had been higher than 7, the cultivation medium was diluted that the $OD_{600}$ value returned to 7, wherein the total volume was 1000 mL 3 L of glucose solution containing 400 g of glucose and 1 L of 4× concentration YP medium were added into the fermenter. The fermenter was kept in a condition that its agitator were rotating at 200 rpm, the temperature was 42° C. and the pH value was 5.

When the condition became stable, 100 mL medium having an OD of 7 was poured in. After 2 minutes of stirring, 20 mL of fermentation suspension was taken as a O-hour sample. 10 mL of the fermentation suspension sample was centrifuged at 14000 rpm for 5 minutes. The supernatant was taken and filtered with a 0.22 μm filter and the concentrations of glucose and ethanol were measured with HPLC. 10 mL of DI water was added to resuspend the pellet. The resuspended suspension was centrifuged at 14000 rpm for 5 minutes, after which the supernatant was removed and 10 mL DI water was added to resuspend the pellet. 1 mL of the suspension was used to measure OD value and the rest was centrifuged at 14000 rpm for 5 minutes and, having the supernatant removed, stored at −80° C. Foregoing sampling and measurement was repeated at time points until the HPLC measured glucose concentration dropped to 0.

Figure 9:
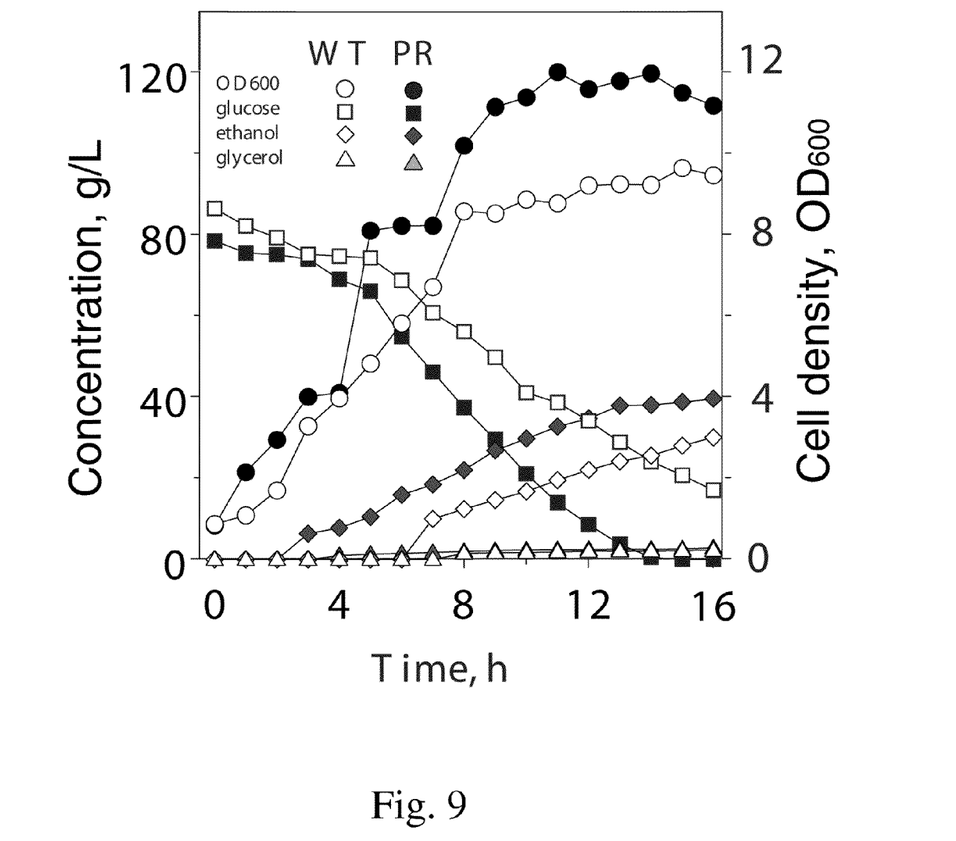
FIG. 9 is a chart of the result of a fermentation experiment using fermenters wherein "WT" represents Kyokai 6 and "PR" represents Kyokai 6-HSP104$^R$/26$^R$ Kan.

As shown in FIG. 9, Kyokai 6-$HSP104^R/26^R$ Kan grew faster than Kyokai 6 and consumed 80 g/L glucose in 14 hours. The ethanol production ratio of Kyokai 6-$HSP104^R/26^R$ Kan based on glucose was as high as 97%.

What is claimed is:

1. A yeast substrain deposited as deposit CCTCC M 2012254 in International Depository Authority China Center for Type Culture Collection (CCTCC), wherein said yeast substrain is a *Saccharomyces cerevisiae* substrain having an upstream regulation region of hsp104 gene which has been replaced with a nucleic acid fragment comprising:
   a first portion comprising
      two FIp/FRT flippase reaction sites, and
      a sequence of an antibiotic resistance gene between the two FIp/FRT flippase reaction sites; and
   a second portion downstream of the first portion and comprising a regulation region of hsp26 gene.

2. A method for making a *Saccharomyces cerevisiae* substrain designated as CCTCC M 2012254 in International Depository Authority China Center for Type Culture Collection (CCTCC), capable of fermenting at a temperature higher than 42° C. to produce ethanol comprising:
   obtaining a plasmid comprising:
      a nucleic acid fragment comprising:
         a first portion comprising
            two FIp/FRT flippase reaction sites and
            a sequence of a antibiotic resistance gene between the two
            FIp/FRT flippase reaction sites, and
         a second portion downstream of the first portion and comprising a regulation region of hsp26 gene; and
      two homologous sequences flanking upstream and downstream of the nucleic acid fragment corresponding to hsp104 gene and a upstream regulation region of the hsp104 gene;
   transforming a *Saccharomyces cerevisiae* strain with the plasmid; and
   screening a *Saccharomyces cerevisiae* substrain the upstream regulation region of the hsp104 gene of which has been replaced with the nucleic acid fragment.

3. The method as claimed in claim 2, wherein the antibiotic resistance gene is the sequence of KanMX6 for resistance against kanamycin.

4. The method as claimed in claim 2, wherein each of the FIp/FRT flippase reaction sites is selected from a group consisting of:
   a FRT sequence and
   a FRT sequence comprising a core region having less than 4 mutated nucleotides.

5. The method as claimed in claim 2, wherein each of the two homologous sequences has a length of 40 base pairs.

6. The method as claimed in claim 2, wherein the *Saccharomyces cerevisiae* strain belongs to *Saccharomyces cerevisiae* Kyokai strain series.

7. A yeast substrain, which is made by the method as claimed in claim 2.

* * * * *

SEQUENCE LISTING

<160> NUMBER OF SEQ ID NOS: 12

<210> SEQ ID NO 1
<211> LENGTH: 54
<212> TYPE: DNA
<213> ORGANISM: Saccharomyces cerevisiae
<220> FEATURE:
<221> NAME/KEY: source
<222> LOCATION: 1..54
<223> OTHER INFORMATION: /mol_type="DNA"
   /note="forward primer for KanMX6"
   /organism="Saccharomyces cerevisiae"

<400> SEQUENCE: 1
gaagttccta ttctctagaa agtataggaa cttcgacatg gaggcccaga atac    54

<210> SEQ ID NO 2
<211> LENGTH: 60
<212> TYPE: DNA
<213> ORGANISM: Saccharomyces cerevisiae
<220> FEATURE:
<221> NAME/KEY: source
<222> LOCATION: 1..60
<223> OTHER INFORMATION: /mol_type="DNA"
   /note="backwards for KanMX6"
   /organism="Saccharomyces cerevisiae"

<400> SEQUENCE: 2
ctcgaggaag ttcctatact ttctagagaa taggaacttc cagtatagcg accagcattc    60

<210> SEQ ID NO 3
<211> LENGTH: 29
<212> TYPE: DNA
<213> ORGANISM: Saccharomyces cerevisiae
<220> FEATURE:
<221> NAME/KEY: source
<222> LOCATION: 1..29
<223> OTHER INFORMATION: /mol_type="DNA"
   /note="forward for HSP26"
   /organism="Saccharomyces cerevisiae"

<400> SEQUENCE: 3
ccgctcgaga tataacctac cataggaca    29

<210> SEQ ID NO 4
<211> LENGTH: 25
<212> TYPE: DNA
<213> ORGANISM: Saccharomyces cerevisiae
<220> FEATURE:
<221> NAME/KEY: source
<222> LOCATION: 1..25
<223> OTHER INFORMATION: /mol_type="DNA"
   /note="backward for HSP26"
   /organism="Saccharomyces cerevisiae"

<400> SEQUENCE: 4
cgcggatccg ttaatttgtt tagtt    25

<210> SEQ ID NO 5
<211> LENGTH: 80
<212> TYPE: DNA
<213> ORGANISM: Saccharomyces cerevisiae
<220> FEATURE:
<221> NAME/KEY: source
<222> LOCATION: 1..80
<223> OTHER INFORMATION: /mol_type="DNA"
   /note="forward for FRTB"
   /organism="Saccharomyces cerevisiae"

-continued

<400> SEQUENCE: 5
gaattcgaag ttcctattct ctagttcgta taggaacttc ccatgggcgg ccgccatatg    60
gacatggagg cccagaatac                                               80

<210> SEQ ID NO 6
<211> LENGTH: 60
<212> TYPE: DNA
<213> ORGANISM: Saccharomyces cerevisiae
<220> FEATURE:
<221> NAME/KEY: source
<222> LOCATION: 1..60
<223> OTHER INFORMATION: /mol_type="DNA"
      /note="backward for FRTB"
      /organism="Saccharomyces cerevisiae"

<400> SEQUENCE: 6
ctcgaggaag ttcctatacg aactagagaa taggaacttc cagtatagcg accagcattc    60

<210> SEQ ID NO 7
<211> LENGTH: 74
<212> TYPE: DNA
<213> ORGANISM: Saccharomyces cerevisiae
<220> FEATURE:
<221> NAME/KEY: source
<222> LOCATION: 1..74
<223> OTHER INFORMATION: /mol_type="DNA"
      /note="forward for 40 homo"
      /organism="Saccharomyces cerevisiae"

<400> SEQUENCE: 7
tttttccaga attttctaga agggttatta attacaatct gaagttccta ttctctagtt    60
cgtataggaa cttc                                                     74

<210> SEQ ID NO 8
<211> LENGTH: 69
<212> TYPE: DNA
<213> ORGANISM: Saccharomyces cerevisiae
<220> FEATURE:
<221> NAME/KEY: source
<222> LOCATION: 1..69
<223> OTHER INFORMATION: /mol_type="DNA"
      /note="backward for 40 homo"
      /organism="Saccharomyces cerevisiae"

<400> SEQUENCE: 8
tcgttagagc cctttctgta aattgcgttt ggtcgttcat gttaatttgt ttagtttgtt    60
tgtttgctt                                                           69

<210> SEQ ID NO 9
<211> LENGTH: 1492
<212> TYPE: DNA
<213> ORGANISM: Saccharomyces cerevisiae
<220> FEATURE:
<221> NAME/KEY: source
<222> LOCATION: 1..1492
<223> OTHER INFORMATION: /mol_type="DNA"
      /note="KanMX6 gene sequence"
      /organism="Saccharomyces cerevisiae"

<400> SEQUENCE: 9
cggatccccg ggttaattaa ggcgcgccag atctgtttag cttgcctcgt ccccgccggg    60
tcacccggcc agcgacatgg aggcccagaa taccctcctt gacagtcttg acgtgcgcag   120
ctcaggggca tgatgtgact gtcgcccgta catttagccc atacatcccc atgtataatc   180
atttgcatcc atacattttg atggccgcac ggcgcgaagc aaaaattacg gctcctcgct   240

```
gcagacctgc gagcagggaa acgctcccct cacagacgcg ttgaattgtc cccacgccgc    300
gcccctgtag agaaatataa aaggttagga tttgccactg aggttcttct ttcatatact    360
tccttttaaa atcttgctag gatacagttc tcacatcaca tccgaacata aacaaccatg    420
ggtaaggaaa agactcacgt ttcgaggccg cgattaaatt ccaacatgga tgctgattta    480
tatgggtata aatgggctcg cgataatgtc gggcaatcag gtgcgacaat ctatcgattg    540
tatgggaagc ccgatgcgcc agagttgttt ctgaaacatg gcaaaggtag cgttgccaat    600
gatgttacag atgagatggt cagactaaac tggctgacgg aatttatgcc tcttccgacc    660
atcaagcatt ttatccgtac tcctgatgat gcatggttac tcaccactgc gatccccggc    720
aaaacagcat tccaggtatt agaagaatat cctgattcag gtgaaaatat tgttgatgcg    780
ctggcagtgt tcctgcgccg gttgcattcg attcctgttt gtaattgtcc ttttaacagc    840
gatcgcgtat ttcgtctcgc tcaggcgcaa tcacgaatga ataacggttt ggttgatgcg    900
agtgattttg atgacgagcg taatggctgg cctgttgaac aagtctggaa agaaatgcat    960
aagcttttgc cattctcacc ggattcagtc gtcactcatg gtgatttctc acttgataac   1020 cttattttg acgaggggaa attaataggt tgtattgatg ttggacgagt cggaatcgca    1080
gaccgatacc aggatcttgc catcctatgg aactgcctcg gtgagttttc tccttcatta   1140
cagaaacggc ttttcaaaa atatggtatt gataatcctg atatgaataa attgcagttt    1200
catttgatgc tcgatgagtt tttctaatca gtactgacaa taaaaagatt cttgttttca   1260
agaacttgtc atttgtatag tttttttata ttgtagttgt tctatttaa tcaaatgtta    1320 gcgtgattta tatttttttt cgcctcgaca tcatctgccc agatgcgaag ttaagtgcgc    1380
agaaagtaat atcatgcgtc aatcgtatgt gaatgctggt cgctatactg ctgtcgattc    1440
gatactaacg ccgccatcca gtttaaacga gctcgaattc atcgatgata tc           1492
```

<210> SEQ ID NO 10
<211> LENGTH: 37
<212> TYPE: DNA
<213> ORGANISM: Saccharomyces cerevisiae
<220> FEATURE:
<221> NAME/KEY: source
<222> LOCATION: 1..37
<223> OTHER INFORMATION: /mol_type="DNA"
     /organism="Saccharomyces cerevisiae"

<400> SEQUENCE: 10
aagggcacat gcggttgtgg cgagtttcat ggtttaa                              37

<210> SEQ ID NO 11
<211> LENGTH: 43
<212> TYPE: DNA
<213> ORGANISM: Saccharomyces cerevisiae
<220> FEATURE:
<221> NAME/KEY: source
<222> LOCATION: 1..43
<223> OTHER INFORMATION: /mol_type="DNA"
     /organism="Saccharomyces cerevisiae"

<400> SEQUENCE: 11
gagcaattta cagaaagggc tctaacgatt ttgacgttgg ctc                        43

<210> SEQ ID NO 12
<211> LENGTH: 34
<212> TYPE: DNA
<213> ORGANISM: Saccharomyces cerevisiae
<220> FEATURE:
<221> NAME/KEY: source
<222> LOCATION: 1..34

```
<223> OTHER INFORMATION: /mol_type="DNA"
     /note="flippase recombinase gene"
     /organism="Saccharomyces cerevisiae"

<400> SEQUENCE: 12
gaagttccta ttctctagaa agtataggaa cttc                              34
```